United States Patent
Su et al.

(10) Patent No.: US 11,846,630 B2
(45) Date of Patent: Dec. 19, 2023

(54) COORDINATELY-ORDERED SINGLE CELLS WITH INDIVIDUAL IDENTITIES FOR HIGH-THROUGHPUT ASSAY

(71) Applicant: Northeastern University, Boston, MA (US)

(72) Inventors: Ming Su, Newton, MA (US); Qingxuan Li, Boston, MA (US); Liyuan Ma, Newton, MA (US); Sidi A. Bencherif, Boston, MA (US); Thibault Colombani, Boston, MA (US)

(73) Assignee: Northeastern University, Boston, MA (US)

( * ) Notice: Subject to any disclaimer, the term of this patent is extended or adjusted under 35 U.S.C. 154(b) by 799 days.

(21) Appl. No.: 16/811,785

(22) Filed: Mar. 6, 2020

(65) Prior Publication Data

US 2020/0284730 A1    Sep. 10, 2020

Related U.S. Application Data

(60) Provisional application No. 62/941,352, filed on Nov. 27, 2019, provisional application No. 62/814,560, filed on Mar. 6, 2019.

(51) Int. Cl.
| | |
|---|---|
| *G01N 33/50* | (2006.01) |
| *G01N 27/02* | (2006.01) |
| *C12M 1/34* | (2006.01) |
| *C12N 13/00* | (2006.01) |
| *G01N 21/64* | (2006.01) |
| *C12M 1/32* | (2006.01) |
| *C12N 5/0783* | (2010.01) |
| *C12N 5/09* | (2010.01) |

(52) U.S. Cl.
CPC ........... *G01N 33/505* (2013.01); *C12M 41/36* (2013.01); *C12N 13/00* (2013.01); *G01N 21/6408* (2013.01); *G01N 21/6428* (2013.01); *G01N 27/02* (2013.01); *G01N 33/5011* (2013.01); *C12M 23/12* (2013.01); *C12N 5/0636* (2013.01); *C12N 5/0693* (2013.01); *G01N 2021/6439* (2013.01)

(58) Field of Classification Search
None
See application file for complete search history.

(56) References Cited

U.S. PATENT DOCUMENTS

2017/0261494 A1* 9/2017 Su ..................... G01N 21/6428

OTHER PUBLICATIONS

Rettig et al., "Large-Scale Single-Cell Trapping and Imaging Using Mmicrowell Arrays" 77 Analytical Chemistry 5628-5634 (Year: 2005).*

An et al., "Single-cell profiling of dynamic cytokine secretion and the phenotype of immune cells," Plos One, 12(8):e0181904 (2017).
Calandri et al., "The role of radiology in the evaluation of the immunotherapy efficacy." Journal of Thoracic Disease, 10(Suppl 13):S1438-S1446 (2018).
Colis et al., "The cytotoxicity of (2)-Iomaiviticin A arises from induction of double-strand breaks in DNA," Nature Chemistry, 6:504-510 (2014).
Couzin-Frankel, "Cancer Immunotherapy," Science, 342(6165):1432-1433 (2013).
Debs et al., "Functional single-cell hybridoma screening using droplet-based microfluidics," PNAS, 109(29):11570-11575 (2012).
Dura et al., "Longitudinal multiparameter assay of lymphocyte interactions from onset by microfluidic cell pairing and culture," PNAS, E3599-E3608 (2016).
Finn, "Immuno-oncology: understanding the function and dysfunction of the immune system in cancer," Annals of Oncology, 23(Supplement 8):viii6-viii9 (2012).
Hosokawa et al., "Microfluidic Device with Chemical Gradient for Single-Cell Cytotoxicity Assays," ACS Analytical Chemistry, 83:3648-3654 (2011).
Kim et al., "A high-throughput microfluidic single-cell screening platform capable of selective cell extraction," Lab Chip, 15:2467-2475 (2015).
Kroll et al., "Cytotoxicity screening of 23 engineered nanomaterials using a test matrix of ten cell lines and three different assays," Particle and Fibre Toxicology, 8(9):1-19 (2011).
Kurschus et al., "Granzyme B delivery via perforin is restricted by size, but not by heparan sulfate-dependent endocytosis," PNAS, 105(37):13799-13804 (2008).
Lawrence et al., "Mutational heterogeneity in cancer and the search for new cancer-associated genes," Nature, 499:214-218 (2013).
Li et al., "Study of the in vitro cytotoxicity testing of medical devices (Review)," Biomedical Reports 3:617-620 (2015).
Mellman et al., "Cancer immunotherapy comes of age," Nature, 480:480-489 (2011).
Mensali et al., "Preclinical assessment of transiently TCR redirected T cells for solid tumour immunotherapy," Cancer Immunology, 68:1235-1243 (2019).
Mervin et al., "Understanding Cytotoxicity and Cytostaticity in a High-Throughput Screening Collection," ACS Chemical Biology, 11:3007-3023 (2016).
Moya-Plana et al., "Evaluation of the efficacy of immunotherapy for non-resectable mucosal melanoma," Cancer Immunology, 68:1171-1178 (2019).
Nishino et al., "Imaging of Cancer Immunotherapy: Current Approaches and Future Directions," Radiology, 290(1):9-22 (2019).
Raser et al., "Noise in Gene Expression: Origins, Consequences, and Control," Science, 309(5743):2010-2013 (2005).
Redman et al., "Quick efficacy seeking trial (QuEST1): a novel combination immunotherapy study designed for rapid clinical signal assessment metastatic castration-resistant prostate cancer," Journal for ImmunoTherapy of Cancer, 6:91 (2018).

(Continued)

*Primary Examiner* — Nancy J Leith
(74) *Attorney, Agent, or Firm* — Dana M. Gordon; Foley Hoag LLP

(57) ABSTRACT

Disclosed is a technology for assaying individual cells, in which the identity of each individual cell in an ordered array is determined from coordinates assigned to it, and can be readout at high throughput with microscope. The method is able to test responses of millions of identical cells in multiple chemical and physical processes with superior statistics power to facilitate deep data mining.

16 Claims, 13 Drawing Sheets

(56) References Cited

OTHER PUBLICATIONS

Ruggeri et al., "Amyloid single-cell cytotoxicity assays by nanomotion detection," Cell Death Discovery, 3:17053 (2017).
Ryan et al., "Single-cell assays," Biomicrofluidics, 5:021501 (2011).
Sambi et al., "Current Challenges in Cancer Immunotherapy: Multimodal Approaches to Improve Efficacy and Patient Response Rates," Journal of Oncology, 2019(Article ID 4508794):1-12 (2019).
Sarkar et al., "Dynamic analysis of immune and cancer cell interactions at single cell level in microfluidic droplets," Biomicrofluidics, 10:054115 (2016).
Tauriainen et al., "Single-cell characterization of in vitro migration and interaction dynamics of T cells expanded with IL-2 and IL-7," Frontiers in Immunology, 6:196 (2015).
Wei et al., "fundamental Mechanisms of Immune Checkpoint Blockade Therapy," Cancer Discovery, 8:1069-1086 (2018).
Wheeler et al., "Microfluidic Device for Single-Cell Analysis," Anal Chem, 75:3581-3586 (2003).
Xia et al., "Microfluidic based immunosensor for detection and purification of carbonylated proteins," Biomed Microdevices, 15:519-530 (2013).
Xia et al., "Single cell patterning for high throughput sub-cellular toxicity assay," Analytica Chimica Acta, 1007:26-32 (2018).
Zhang et al., "Multisensor-integrated organs-on-chips platform for automated and continual in situ monitoring of organoid behaviors," PNAS, E2293-E2302 (2017).

* cited by examiner

COORDINATELY-ORDERED SINGLE CELLS WITH INDIVIDUAL IDENTITIES FOR HIGH-THROUGHPUT ASSAY

RELATED APPLICATIONS

This application claims the benefit of priority to U.S. Provisional patent application Ser. No. 62/814,560, filed Mar. 6, 2019; and U.S. provisional patent application Ser. No. 62/941,352, filed Nov. 27, 2019.

GOVERNMENT SUPPORT

This invention was made with government support under Grant Number EB016572 awarded by the National Institutes of Health, and under Grant Number 1847843 awarded by the National Science Foundation. The government has certain rights in the invention.

BACKGROUND

In vitro toxicity assays play an important role in understanding biological mechanisms, detecting diseases, and screening drugs and therapeutics. Cited references 1-6. Toxicity assays (i.e., cytotoxicity and genotoxicity) are often carried out by stimulating cells incubated in microwells, which yield results based on average response of cells in the same well. However, cell populations are heterogeneous, and differentiating responses of individual cells in large populations become crucial. Cited references 7 and 8. The most commonly used techniques for single cell studies are flow cytometry, capillary electrophoresis, microscopy, and patterned cell arrays. Cited references 9-13. However, a major drawback of current single cell assays is that the response of the same cells in multiple processes cannot be tracked. The data presented in flow cytometry does not indicate the responses of the same cells. This lack of cell identification significantly hinders the uses of single cell technology in comparison to current cell ensemble.

Cancer immunotherapy represents a new frontier in cancer therapies that has been promising for many years. Cited references 15-19. Taking advantage of artificial stimulation, cancer immunotherapy works by boosting immune system to better recognize and eliminate cancer cells. The tumor clearance efficacy is fundamentally based on individual immune system and the interaction between immune cells and cancer cells. However, the efficacy of immunotherapy is often unpredictable due to tumor heterogeneity, immunosuppressive tumor microenvironments, and variations in patient immune responses. Cited references 20-25. In addition, the lack of known Tumor-specific Antigen (TSA) and the prohibitive cost of cancer immunotherapy drugs dramatically hamper their development. Therefore, there is an urgent need to develop better models to screen immune cell response and evaluate immunotherapeutic strategy at a single tumor cell level. Current single cell analysis has emerged as a powerful tool in vitro for immunotherapeutics in order to accurately study immune cell responses, but they are limited to study one single aspect of these responses with a low sample population. A new method that can comprehensively investigate the overall function of immune cells is therefore needed, which should allow combined study of cytokine secretion detection with quantified cytotoxicity. Cited references 26-29.

SUMMARY

Disclosed is a new technology for single cell assay, in which the identity of each individual cell in an ordered array is determined from coordinators assigned to it, and can be readout at high throughput with a microscope. This method is able to test responses of millions of identical cells in multiple chemical and physical processes with superior statistics power to allow deep data mining.

A microwell array has been developed as a high-throughput in vitro platform to quantify T cell cytotoxicity, T cell cytokine secretion, and T cell-tumor cell interaction in real time. Thousands of cancer cells (i.e., murine B16-OVA melanoma cells) were co-cultured individually with different T cell (OT-1) ratio in microwells at various diameters (30, 50, and 100 µm). Cancer cell viability in each well at a single cell level was monitored by fluorescence time-lapse microscopy. Furthermore, a mathematic model was developed to quantify the relationship between T cell-mediated cytotoxicity, killing efficiency, and cytokine secretion, which provides a more precise understanding of immune-cancer cell interactions and computational prediction of T cell cytotoxicity.

Commercial applications of the technology include: screening drugs and therapeutics for treatments of cancers and other diseases; mini-drug testing at point-of-use to identify the best available treatment for individual patient for personalized medicine; and probing cell toxicity (both cytotoxicity and genotoxicity) at identical cell level.

In some embodiments, the present disclosure relates to a method of determining a response of individual cells to stimuli, comprising:
(a) providing a plurality of cells distributed on a grid;
(b) exposing the plurality of cells to two or more stimuli; and
(c) measuring a response of one or more cells of the plurality of cells to the stimuli.

In some embodiments, the present disclosure relates to a method of measuring interactions of individual cells, comprising:
(a) providing a plurality of first cells distributed on a grid;
(b) exposing the plurality of first cells to a plurality of second cells; and
(c) measuring the interaction between one or more first cells and one or more second cells.

DETAILED DESCRIPTION

As used herein, the term "stimulus" refers to a physical, chemical, or biological stimulus that is applied to the cell. For example, the stimulus can be electromagnetic radiation, such as microwave radiation, infrared radiation, UV or visible light radiation, X-ray radiation, or γ-radiation. Alternatively, a stimulus can be a chemical compound, such as a chemotherapy agent. Alternatively, a stimulus can be a cell, a drug formulation, or an environmental toxin.

As used herein, the term "capture agent" refers to an agent, such as a chemical compound, a protein, an antibody, a polycation, or a molecule comprising one or more positively charged groups or cell-attracting moieties, that can bind to a molecule secreted by a cell. A capture agent can be a molecule that specifically binds to one or more antigens expressed on cell surfaces (such as folic acid).

Figure 1:
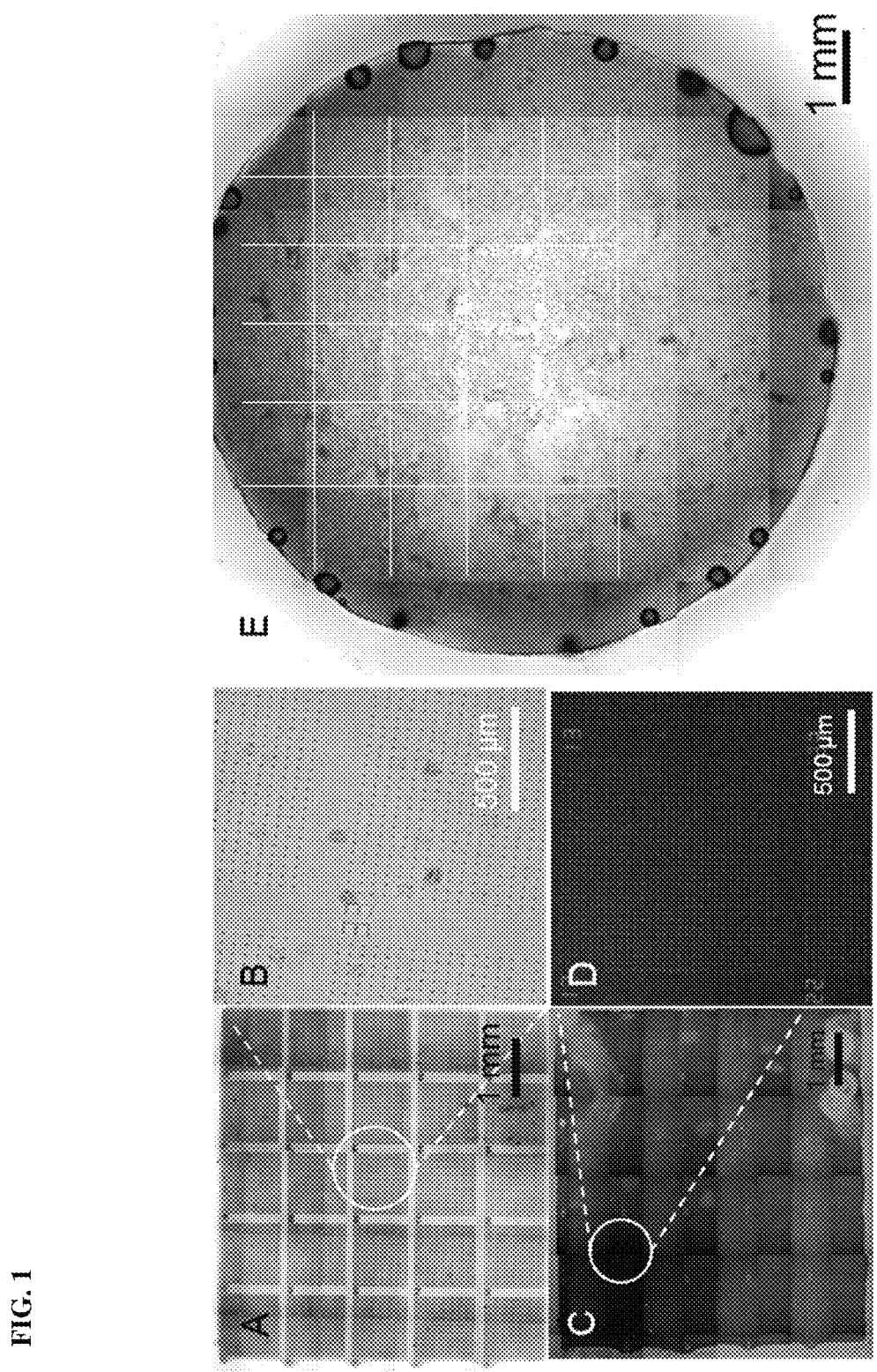
FIG. 1 shows the pattern in PDMS stamp without ink (panels A-B), the pattern prepared by ink after transferring onto PEG coated glass slide (panels C-D), and after adding cells (panel E).

FIG. 1 shows the pattern in PDMS stamp without ink (A-B) and the pattern prepared by ink after transferring onto PEG coated glass slide (C-D). The PEG coated glass slide can make sure cells being adhered on specific area with pattern. The green fluorescence in C shows successful transfer of coordinated pattern. The number represents different coordinated square, which is made of 900 dots. Each dot in coordinated square can attract one cell via electrostatic interaction. After adding cells and washing unbounded cells, the cell occupancy is determined to be 91% on the substrate.

Figure 2:
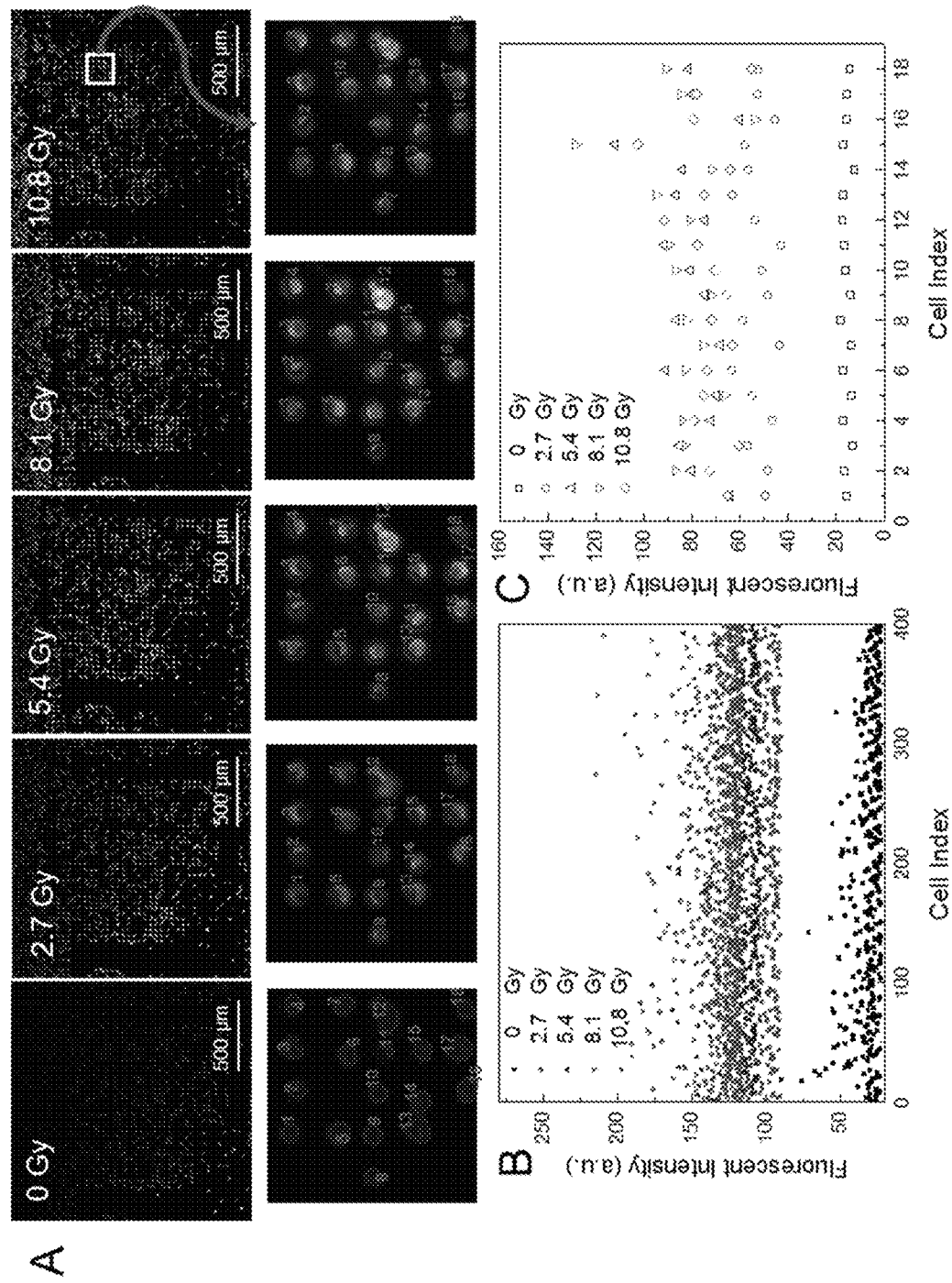
FIG. 2 shows identical cell analysis upon different X-ray radiation dose treatment (panels A-C).

CellROX™ Orange Reagent was applied on the coordinate cell pattern. This cell-permeant dye is non-fluorescent while in a reduced state and exhibits bright orange fluorescence upon oxidation by reactive oxygen species (ROS), with absorption/emission maxima of ~545/565 nm. Environmental stress (e.g. UV or X-ray) can cause increase of reactive oxygen species (ROS) signal. In this coordinate system, cells at the same locations could be easily found after several steps of X-ray exposures (FIG. 2, panel A). The intensity after each exposure was calculated by MATLAB which is shown in FIG. 2, panel B. Hundreds of cells could be labeled according to fluorescent intensities. The data obtained from identical cells after different exposure shows the same trend as those from a 24 well plate, which proves the reliability and accuracy of coordinate cell pattern in cytotoxicity analysis. The picture was cropped to analyze identical cells. Each cell was uniquely numbered (indexed) and identical cells are identified by the same cell index number (FIG. 2, panel C), in which the diverse sensitivity of HeLa cells to X-ray radiation is observed. By locating cells onto coordinated pattern, both the statistical data and the identical cell data could be obtained, and the sensitivity of each cells to X-ray exposure could be studied.

Figure 3:
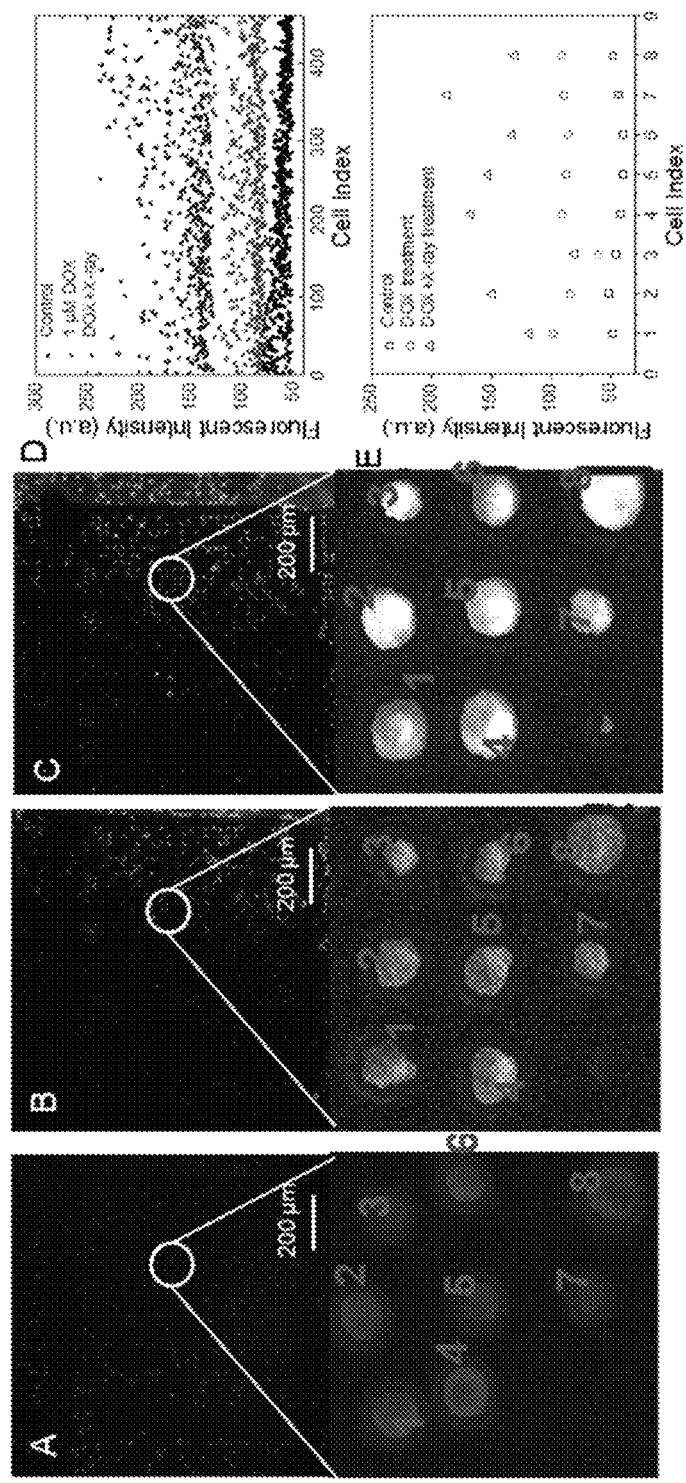
FIG. 3 shows identical cell responses after combining chemotherapy with radiotherapy. The controlled group (panel A) without any treatment. Cells incubated with 1 µM doxorubicin for 6 hours (panel B) and then exposed to X-ray for 10.8 Gy (panel C).

FIG. 3 shows identical cell responses after combining chemotherapy with radiotherapy. After incubating with 1 µM doxorubicin for 6 hours, the ROS orange signal increases. The cell was then exposed to X-ray, the intensity shows much higher level of damage than that of doxorubicin alone. FIG. 3, panel E shows that cells show different sensitivity to doxorubicin and X-ray, and this method can be used to determine cell heterogeneity.

Figure 4:
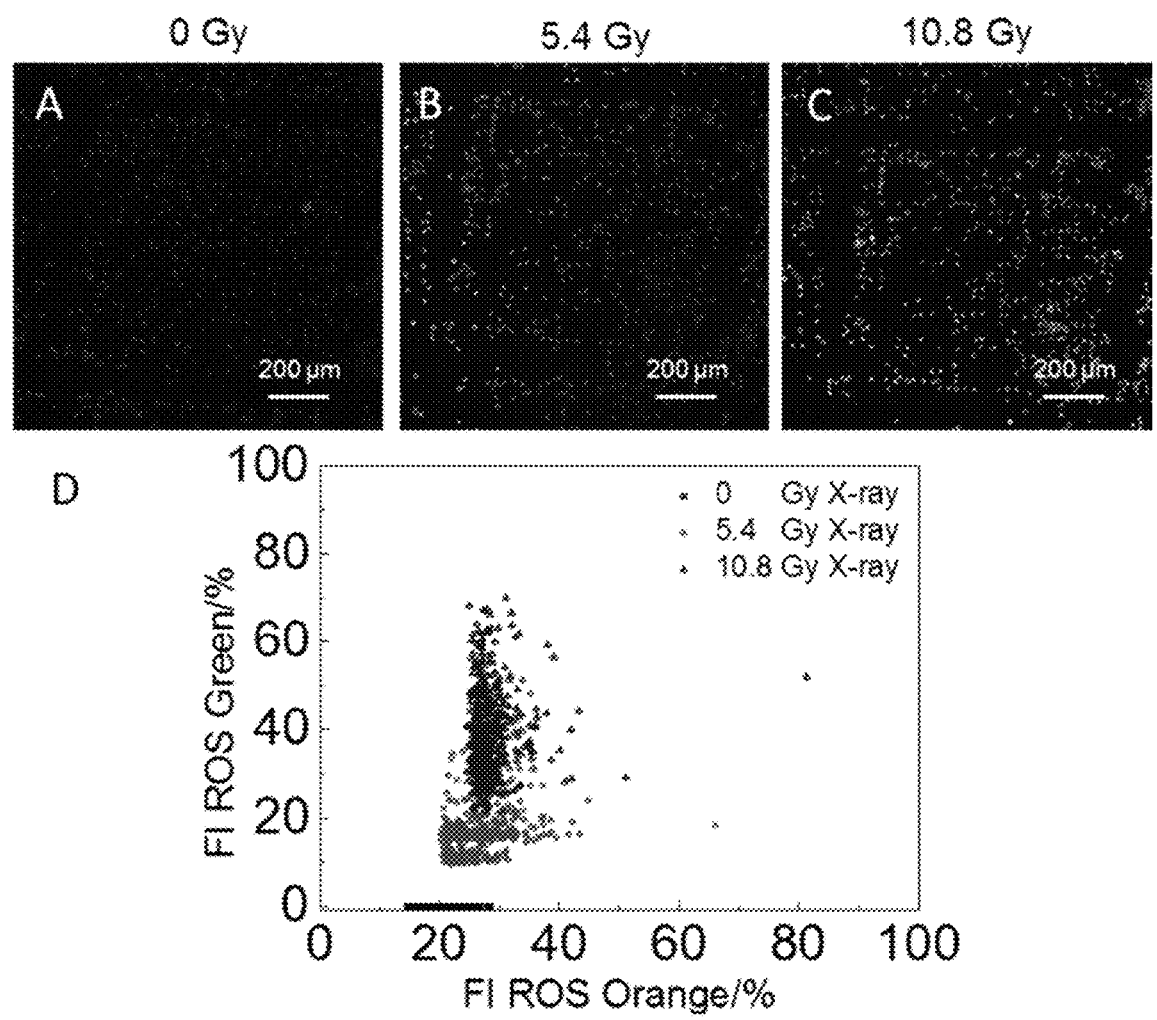
FIG. 4 shows double staining merged images of green and orange fluorescent light in coordinated cell pattern upon different X-ray radiation dose (panels A-C) and a scatter plot of fluorescent intensity of orange and green light (panel D).

Coordinated cells can be stained with two fluorescence dyes. FIG. 4 shows co-staining of coordinated cells with ROS orange and green dyes—CellROX™ Orange Reagent and CellROX™ Green Reagent. CellROX™ Green Reagent is a fluorogenic probe for measuring oxidative stress in live cells. The cell-permeant dye is weakly fluorescent while in a reduced state and exhibits bright green photostable fluorescence upon oxidation by reactive oxygen species (ROS) and subsequent binding to DNA, with absorption/emission maxima of ~485/520 nm. The heterogeneity towards different treatment and the damage level could be seen between nucleus and cytoplasm. Orange light and green light intensity were represented on X-axis and Y-axis, respectively. Both orange and green signals increase with X-ray dosage. The relative strong green color intensity upon radiation suggests that nucleus experiences more damage than the cytoplasm upon X-ray radiation.

Besides statistical analysis, a few cells were cropped and analyzed at identical cell level in real time. The same number of each symbol in FIG. 5, panel E, represent the same cell. By calculating the fluorescent intensity in each cell, the varying responses of each cell to X-ray can be determined, as well as the responses of the identical cells to multiple X-ray exposures.

Quantitative Single Cell Assay for Immune Response Monitoring (qSCAIRM)

In some embodiments, the present disclosure relates to a microwell array, which can be used as a high-throughput in vitro platform to quantify T cell cytotoxicity, T cell cytokine secretion, and T cell-tumor cell interaction in real time. In some embodiments, thousands of cancer cells (i.e., murine B16-OVA melanoma cells) were co-cultured individually with different T cell (OT-1) ratio in microwells at various diameters (30, 50, and 100 µm). In further embodiments, cancer cell viability in the wells at a single cell level can be monitored, for example, by fluorescence time-lapse microscopy. In some embodiments, the relationship between T cell-mediated cytotoxicity, killing efficiency, and/or cytokine secretion was quantified. This approach allows a more precise understanding of immune-cancer cell interactions and computational prediction of T cell cytotoxicity.

The methods, devices, and/or materials of the present disclosure can be applied for one or more of the following:
- CD8 T cell cytotoxicity and cytokine secretion can be quantified during interaction of T cells with cancer cells (B16 melanoma cells).
- Immunotherapeutic efficacy based on different T cells with modified receptors (CAR T cell, OT-1 cell) can be assessed.
- Real-time and long-time observation of T cell-cancer cell interactions at single cell level
- Controllable cell occupancy and loading number by tuning the microwell size.
- Over thousands of cancer cells' behavior can be tracked simultaneously while interacting with T cells.
- Immune cell-immune cell interactions.
- Screening of immune cells for single cell genomics/proteomics.
- Discovery of new biomarkers.

The present disclosure includes embodiments to a multi-functional device: evaluation of cell-cell interactions, assessing T cell-associated cytotoxicity, and quantitative immunoassay can be integrated in one single device, and ultimately boosting productivity while reducing costs.

In some embodiments, the multifunctional device, e.g., the microwell device is based on low-cost materials (e.g., PDMS) with simple fabrication steps.

Figure 6:
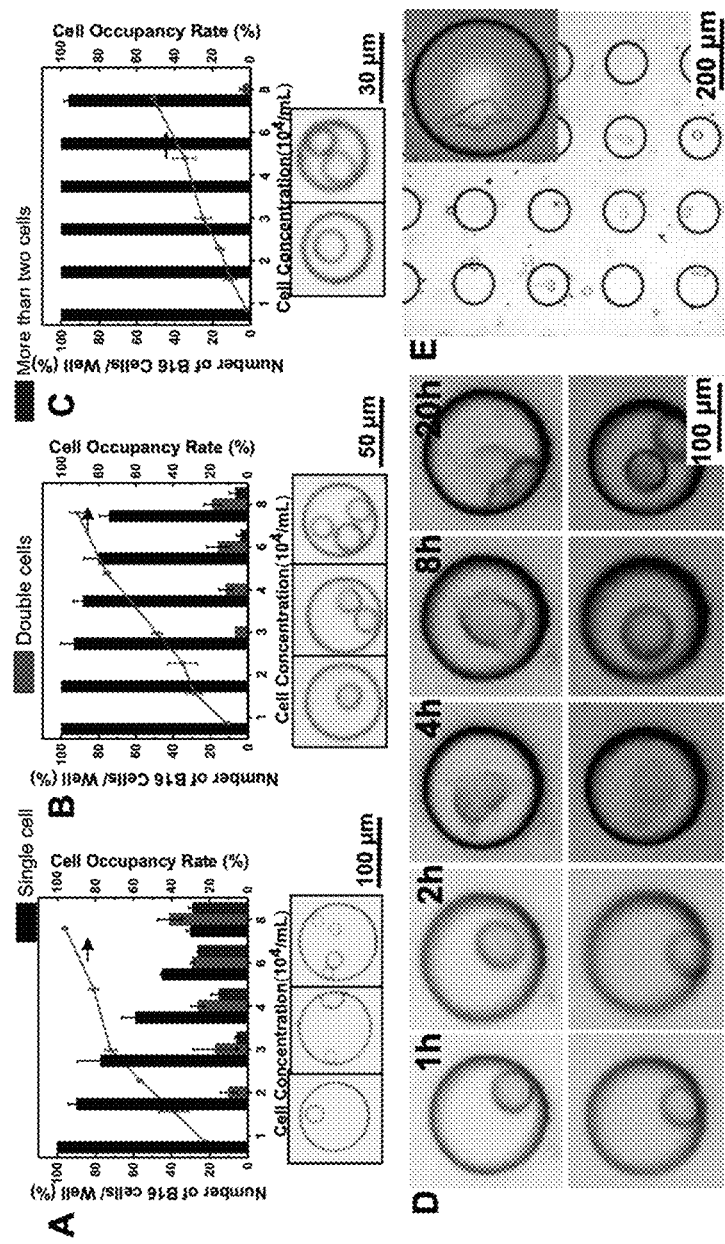
FIG. 6 shows images demonstrating occupancy rate and cell viability of B16 cells in a microwell array, panels A-E. Panels A-C show single cell (black), double cells (red) and more than three cells (blue) occupying each well under different cell concentrations with microwell diameter of 100 µm (A), 50 µm (B), and 30 µm (C). Optical images of microwell array with different number of cells inside are shown in panels A-C. A series of optical images of B16 cells at different time points is shown in panel (D). Cell survivability of B16 cells in PDMS microwell system after 24 hours. The bright field, Calcein AM green light, and merged image in 100 µm well systems (E). Enlarged images of cell morphology in microwell are inserted in the bottom-left corner of merged pictures.

FIG. 6 shows the occupancy of B16 cancer cells in microwells of different diameter (30, 50, and 100 µm) in DMEM medium. The percentages of microwells occupied by cells are shown in FIG. 6, panels A-C, where black, blue and red columns show the percentages of one, two and three cells per well, respectively, at the same cell seeding density. The 100 µm diameter microwell has 90% occupancy, in comparison to 50% for 30 µm diameter microwell at the cell concentration of 80,000/mL. The adhesion and division of identical cells are monitored over a course of 20 hours (FIG. 6, panel D), where cells attach on surface and stretch to 40-50 µm after 4 hours, and start to divide after 20 hours, indicating cell cycles of B16 cells remains the same after seeding in microwell. FIG. 6, panel E, shows cell viability after staining with Calcein AM and propidium iodide, where green color shows a majority of cells still survive 24 hours after settling in well.

Figure 7:
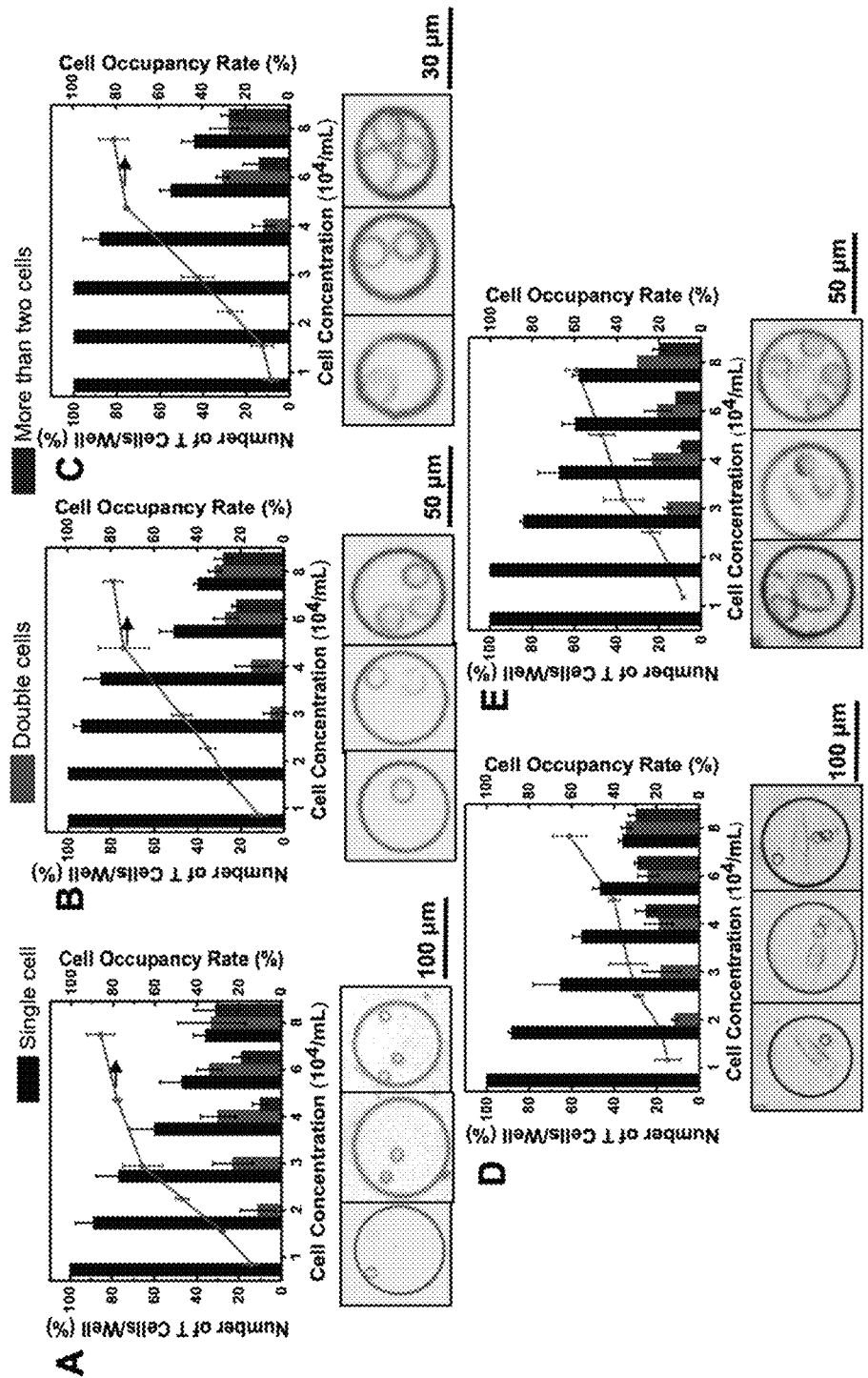
FIG. 7 shows images demonstrating T cell occupancy rate in microwell array and co-culture assessment in panels A-E. Panels A-C show single cell (black), double cells (red) and more than three cells (blue) occupying each well under different cell concentrations with microwell diameter of 100 µm (A), 50 µm (B), and 30 µm (C). T cells occupancy rate in each well occupied with B16 cells in co-culturing condition, evaluated in 100 µm microwell system (D) and 50 µm microwell system (E). Optical images of microwell array with different number of cells are shown below (A)-(E).

FIG. 7, panels A-C, shows cell occupancy of OT-1 cells in three microwells (30, 50, and 100 µm in diameter), where the occupancy rate of OT-1 cells is proportional to cell concentration, with the maximum of 80% at an OT-1 cell concentration of 80,000/mL. FIG. 7, panels D-E, shows the occupancy of co-cultured OT-1 cells in 100 µm microwells, where three optical images below show B16 cells with various number of OT-1 cells. After culturing in RPMI for 6 hours and contacting with OT-1 cells, B16 cells still maintain their spindle shape, indicating good adaption and normal metabolism of B16 cells in RPMI in the presence of OT-1 cells.

Figure 8:
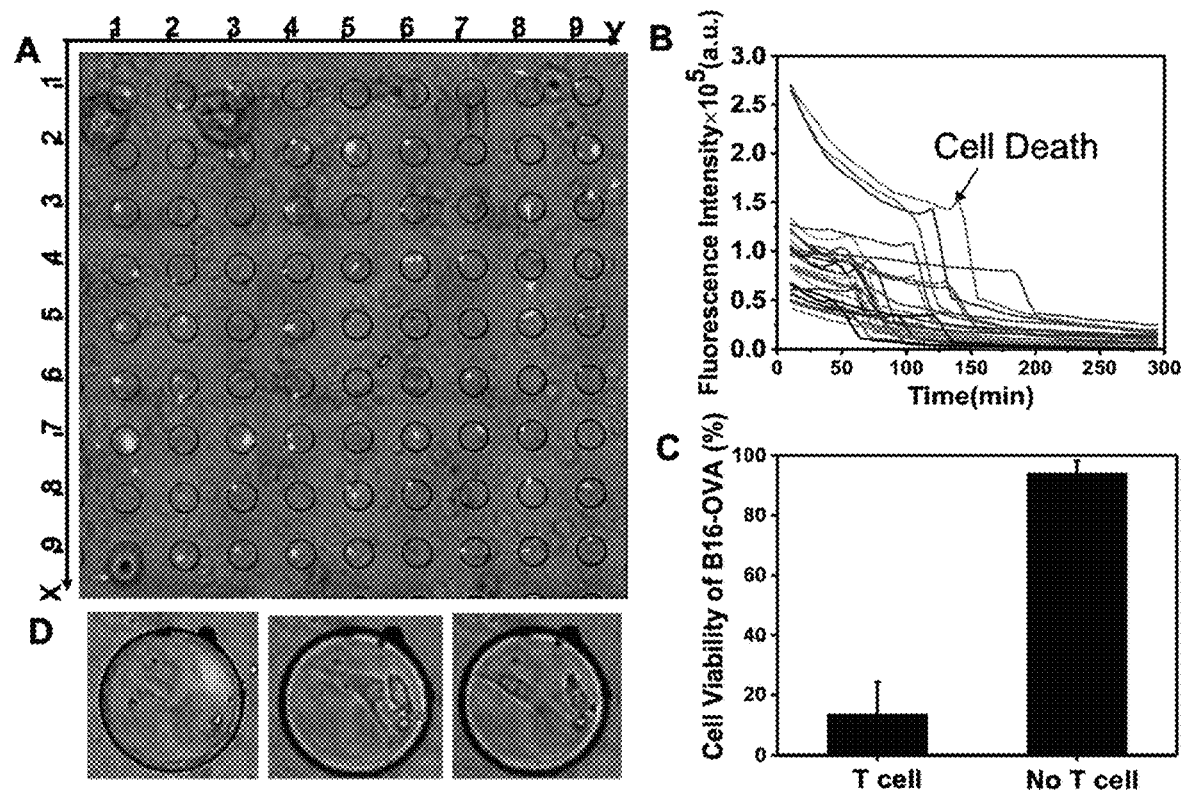
FIG. 8 shows time-lapse observation and OT-1 cell cytotoxicity, panels A-D. 3×3 tilted images of co-culturing B16-OVA and OT1 cells (A), merged by optical and green channel. B16-OVA cells are stained by CFSE green cell tracker. Fluorescence intensity of each B16-OVA cell over time (B). Cell viability of B16-OVA with and without OT-1 cells (C). The coordinate (index) of each cell is represented by (X, Y). Time-lapse images of B16 and B16-OVA cells interacting with OT-1 cells (D)

FIG. 8, panel A, shows a merged large-scale image of co-cultured B16-OVA and OT-1 cells in 100 µm microwells, where B16-OVA cells are stained with green fluorescence dye and their interaction with OT-1 cells is tracked over time with time lapse video. The intensity of each cancer cell is derived from green fluorescence image with MATLAB to quantify its viability. FIG. 8, panel B, shows the intensities of fluorescent signals over time for all cells in FIG. 8, panel A. The fluorescence signal intensity of cancer cell in each well reduces, likely due to cytokines secreted from OT-1 cells. A sudden change in the slope of the fluorescence signal is used to indicate the status (live or dead) of the cancer cell. The time taken to achieve the sudden drop in each line is identified as the killing time. The killing time varies for B16-OVA cells from less than 60 min (cell at location 8, 3) to 200 min (cell at location 9, 7). The variation in killing time reflects the high level of heterogeneity of OT-1 cytotoxicity on cancer cells. FIG. 8, panel C, shows the viabilities of B-16-OVA cells in the presence of OT-1 cells, which is 6 times lower than that without OT-1 cells. In order to evaluate T cell-cancer cell recognition based on ovalbumin, B16 cells without expression of ovalbumin co-cultured with B16-OVA (stained with green fluorescence) are shown in FIG. 8, panel D. During the interaction for 6 hours, B16 cell still attached on surface and stay alive while B16-OVA cell is died according to fluorescence loss due to recognition of OT-1 cells, meaning OT-1 cells can only recognize B16 with expression of ovalbumin and trigger attack.

Figure 9:
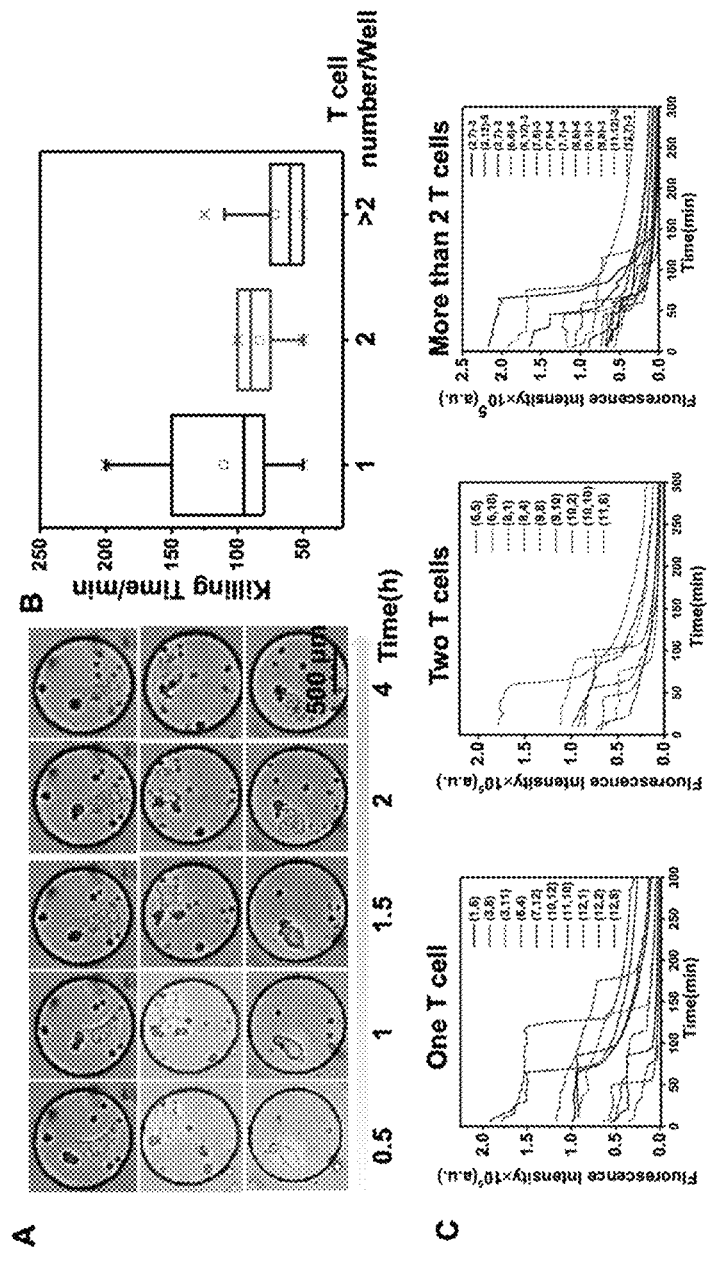
FIG. 9 shows evaluation of number-dependent OT-1 cytotoxicity at a single cancer cell level, panels A-C. B16-OVA morphology and fluorescence loss at different time point (A). Average killing time versus different T cell number (B). Fluorescence loss of B16-OVA with different T cells longitudinally over time (C).
Figure 10:
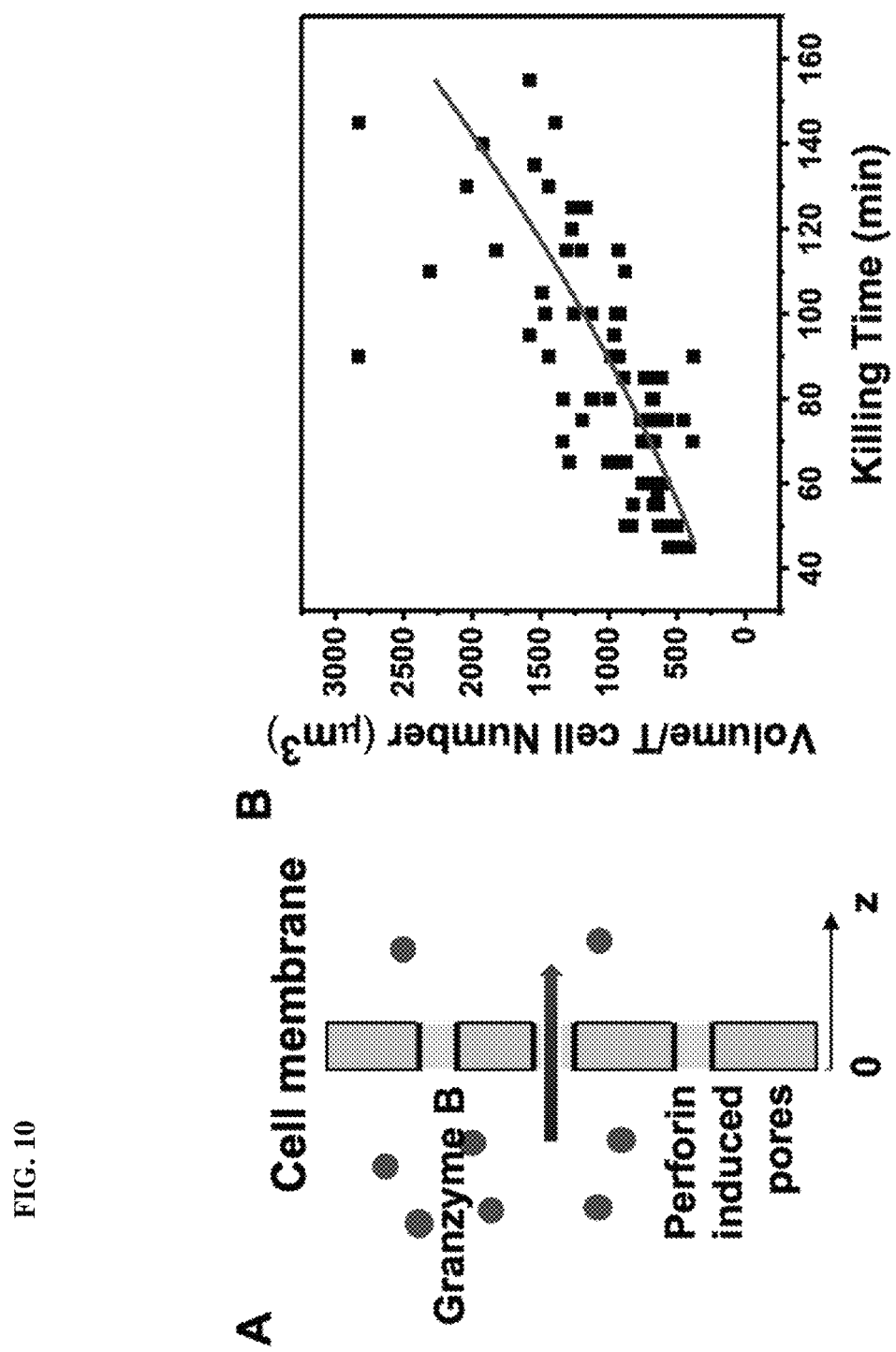
FIG. 10 shows mass transfer model of Granzyme B diffusion through cell membrane, panels A-B. Scheme of Granzyme B diffusion during B18-OVA and OT-1 cell interaction (A). Normalized contacting area of each T cell corresponding with killing time with non-linear fitting (B).

FIG. 9, panel A, shows time-dependent fluorescence intensity of single cancer cell interacting with one, four, and five OT-1 cells. B-16 OVA cell interacting with one OT-1 cell died after 2 hours, and that interacting with five OT-1 cells died after 1.5 hours. The death of cancer cell is confirmed from dye diffusion and fluorescence signal loss. FIG. 9, panel B, shows the fluorescence of each B16 OVA cell versus time when one, two and more OT-1 cells are distributed in each microwell. The coordinate of each cell is shown in the upper corner of each figure, and the actual numbers of OT-1 cells in the case of more than two OT-1 cells are given after coordinates. The killing time for OT-1 cells varies from 50 to 200 min, and that for two OT-1 cells varies from 50 to 100 min, compared to that for more OT-1 cells mainly at 60 min. FIG. 9, panel C, is the box graph showing average killing time of single B16-OVA cell for different number of OT-1 cells. The lower and upper boundary of box are determined at 25% and 75% of data distribution, which means a majority of cancer cells interacting with one T cell die at 80~150 min, while a cancer cell interacting with more than two cells has shorting killing time (55~75 min). The shorter killing time for more OT-1 cells is a strong evidence that the killing effect strongly depends on the number of OT-1 cells for single cancer cells, or the ratio of OT-1 cells to cancer cells.

Upon contact, OT-1 cells recognize ovalbumin expressed on the surface of B16-OVA and secrete cytokines. Perforin can create pores on a cell membrane and lead to diffusion of dye. Granzyme B can diffuse through pores into cytoplasm to induce apoptosis. In order to understand the physical image behind interaction of B16-OVA cells and OT-1 cells, a simple model based on mass transfer through a cell membrane was established. Assuming the area of pores created by Perforin is constant and during the formation of the pores no Granzyme B is diffusing inside cells due to molecular crowding. The concentration of Granzyme B between cell pairs (OT-1 and B16-OVA cells) is considered as constant near the outside surface of the cell membrane. The diffusion of Granzyme B through pore in the cell membrane is given as:

$$J = -D\frac{dC_G}{dz} \quad (1)$$

According to Fick's Second Law for one-dimensional and unsteady state diffusion, $$\frac{\partial C_G}{\partial t} = D\frac{\partial^2 C_G}{dz^2} \quad (2)$$

where $C_G$ is the concentration of Granzyme B and z is the thickness of the cell membrane, which is far less than cell diameter and there is no Granzyme B initially existing inside cells. The initial condition is given as $C_G=0$ at $t\leq 0$ and $z\geq 0$. The boundary conditions are given as $C_G=C_{G0}$ at $t\geq 0$, $z=0$ and $C_G=0$ at $t\geq 0$, $z\to\infty$. Here, since cell size is far more than the cell membrane, z to infinite is equal to z to the center of cell.

The result of PDE is given by dimensionless substitution and error function:

$$\frac{C_G}{C_{G0}} = \text{erfc}\left[\frac{z}{2\sqrt{Dt}}\right] \sim 1 - \frac{\exp\left(-\frac{z^2}{4Dt}\right)}{\sqrt{\pi}\frac{z}{2\sqrt{Dt}}} \quad (3)$$

Get back to equation (1) and determine the equation for Granzyme B mass flux in the cell membrane:

$$J = \sqrt{D/\pi t}\,\exp(-z^2/4Dt)C_{G0} \quad (4)$$

Flux across the interface at z=0 is $$J|_{z=0} = \sqrt{D/\pi t}\,C_{G0} \quad (5)$$

Equation (5) is the mass flux of Granzyme B through one pore in the cell membrane. Assuming the total pores in the cell membrane are proportional to Perforin and T cell numbers, the total mass transfer through pores is represented as a sum of mass flux through each pore.

Therefore, the total mass flux of Granzyme B through the cell membrane during a time period of t is given:

$$M_B = \Sigma_1^i N_T \delta A \int_0^t J\,dt \quad (6)$$

The toxic concentration of Granzyme B to kill a cell is given as:

$$C_{dead} = \frac{M_B}{V_0} = \frac{\Sigma_1^i N_{T_i} A \int_0^t J\,dt}{V_0} = \frac{2\delta N_T A\sqrt{D/\pi}\,C_{G0}}{3V_0} t^{3/2} \quad (7)$$

where $N_T$ is T cell number, A is intersection area of pore created by Perforin, $V_0$ is the volume of the cancer cell, t is the time for T cells to kill the cancer cell, $C_{G0}$ is the initial concentration of Granzyme B, D is the mass transfer coefficient in the cell membrane.

The killing concentration of Granzyme B is normalized by the ratio between the area of an attached cancer cell and the number of OT-1 cells in each well and is given as:

$$\frac{V_0}{N_T} = \frac{2\delta A\sqrt{D/\pi}\,C_{G0}}{3C_{dead}} t^{3/2} = \varphi t^{3/2} \quad (8)$$

where $$\varphi = \frac{2\delta A\sqrt{D/\pi}\,C_{G0}}{3C_{dead}}$$

Figure 5:
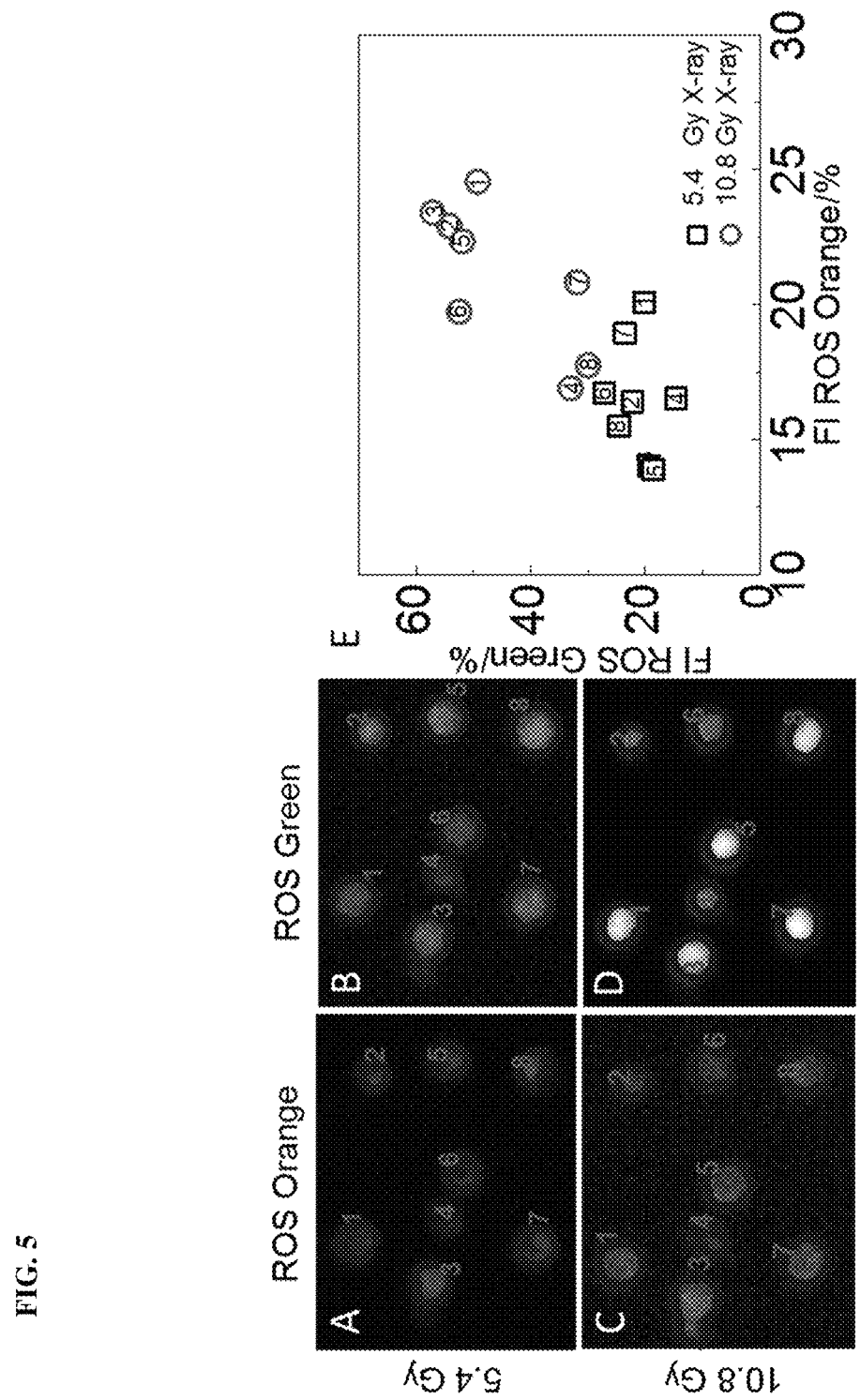
FIG. 5 shows identical cell analysis upon double staining method. ROS orange signal under 5.4 Gy (A) and 10.8 Gy (C) as well as ROS green signal under 5.4 Gy (B) and 10.8 Gy (D). Double staining analysis in identical cell level (E).

The interaction area is normalized as the ratio between the area of an attached cancer cell and the number of OT-1 cells in each well. The intersection of area is around 10 nm, mass transfer coefficient is assumed to be $10^{-4}$ mm$^2$s$^{-18}$. The normalized interacting area ($V_0/N_T$) in microwell system versus time is shown in FIG. 5, where the size of each cancer cell is measured by pixel and the killing time is counted at the fluorescence drop point. Each dot represents each cancer cell interacting with different number of T cells. Red line in FIG. 6 is the nonlinear fitting under equation $Y=AX^{3/2}$. The standard error is at 0.048 and coefficient ($\varphi$) of the independent variable is at 1.188. Given A=10 nm, D=$10^{-4}$ mm$^2$s$^{-1}$, if the concentration of Granzyme B $C_{G0}$: $C_{dead}$=1000:1, $\delta$ can be determined as $10^2$, which means one T cell can create $10^2$ pores on cell membrane induced by antigen recognition.

Figure 11:
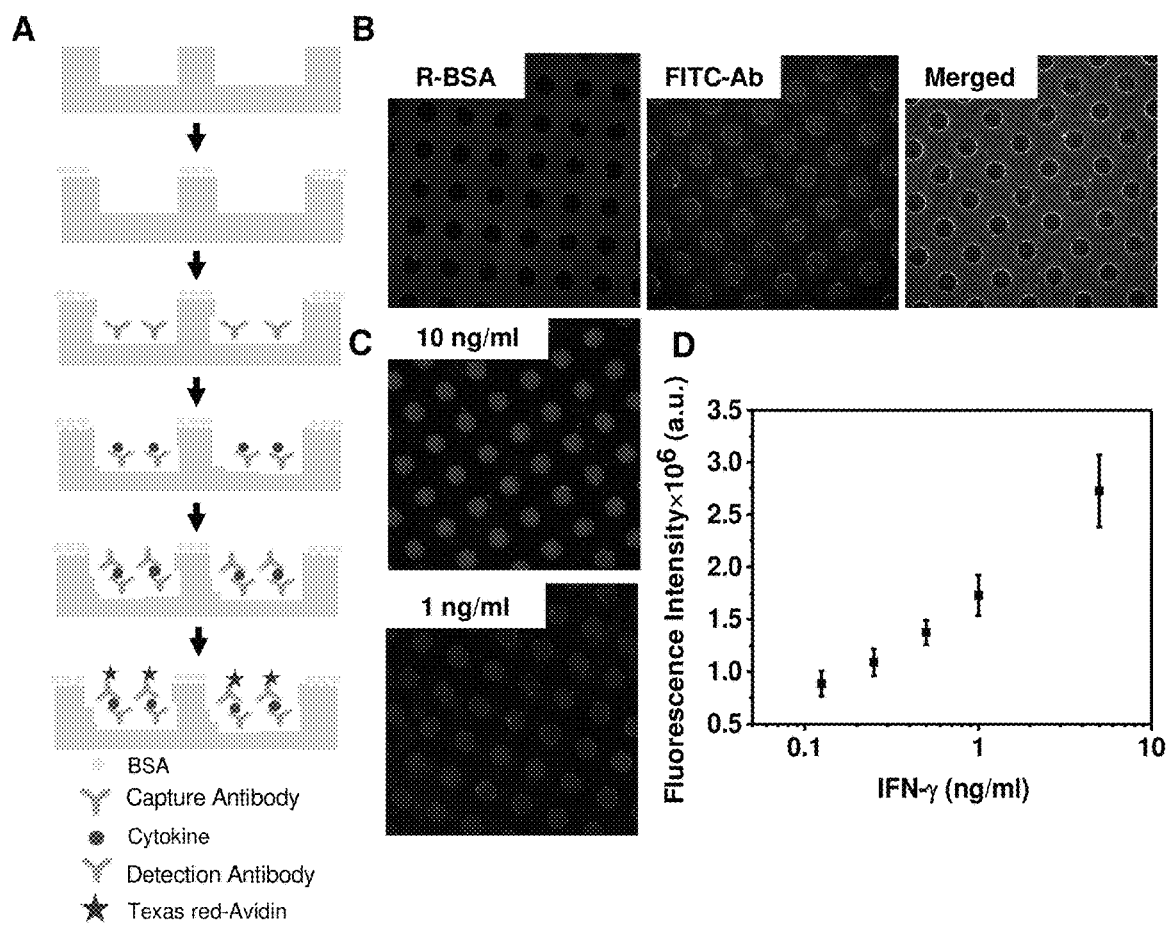
FIG. 11 shows surface modification and immunoassay of microwells. The schematic illustration of surface modification (A). BSA saturation and fluorescence enhancement inside microwells (B). Fluorescence images of immunoassay based on Avidin Texas red fluorescence (C) and standard curve of fluorescence versus concentration (D).

Surface of the microwells can be chemically modified with capture agents, such as antibodies, to detect cytokines secreted by T cells during the T cell-cancer cells interaction. The modification process is represented in FIG. 11, panel A, demonstrating how the top layer of a PDMS chip was firstly coated by BSA and then the capture antibody for specific cytokine molecules was absorbed on the surface. The cytokine detection is based on ELISA sandwich structure and quantified based on the fluorescence intensity of Avidin Texas red. Due to the existence of BSA on the top layer, the majority of antibodies were only absorbed on the inner surface of the microwells (bottom and inside wall of microwell), which enhanced capturing signals and reduced background. The location of the capture antibody after BSA saturation was indicated using Rhodamine-BSA and FITC-Antibody and shown in FIG. 11, panel B, in which BSA only covered the top layer of microwell and the green fluorescent capture antibody was mainly present inside the microwells after BSA saturation, enhancing the signals from the microwells. The fluorescence images of interferon-γ at two concentrations are shown in FIG. 11, panel C, and the standard curve of fluorescence versus interferon-γ concentration is presented in FIG. 11, panel D. According to the standard curve, imaged-based ELISA using the microwells detected a wide range of the cytokine concentrations from 0.1 ng/mL to 5 ng/mL, and the concentrations determined based on fluorescence intensity ranged from $0.8 \times 10^5$ to $2.7 \times 10^5$.

Figure 12:
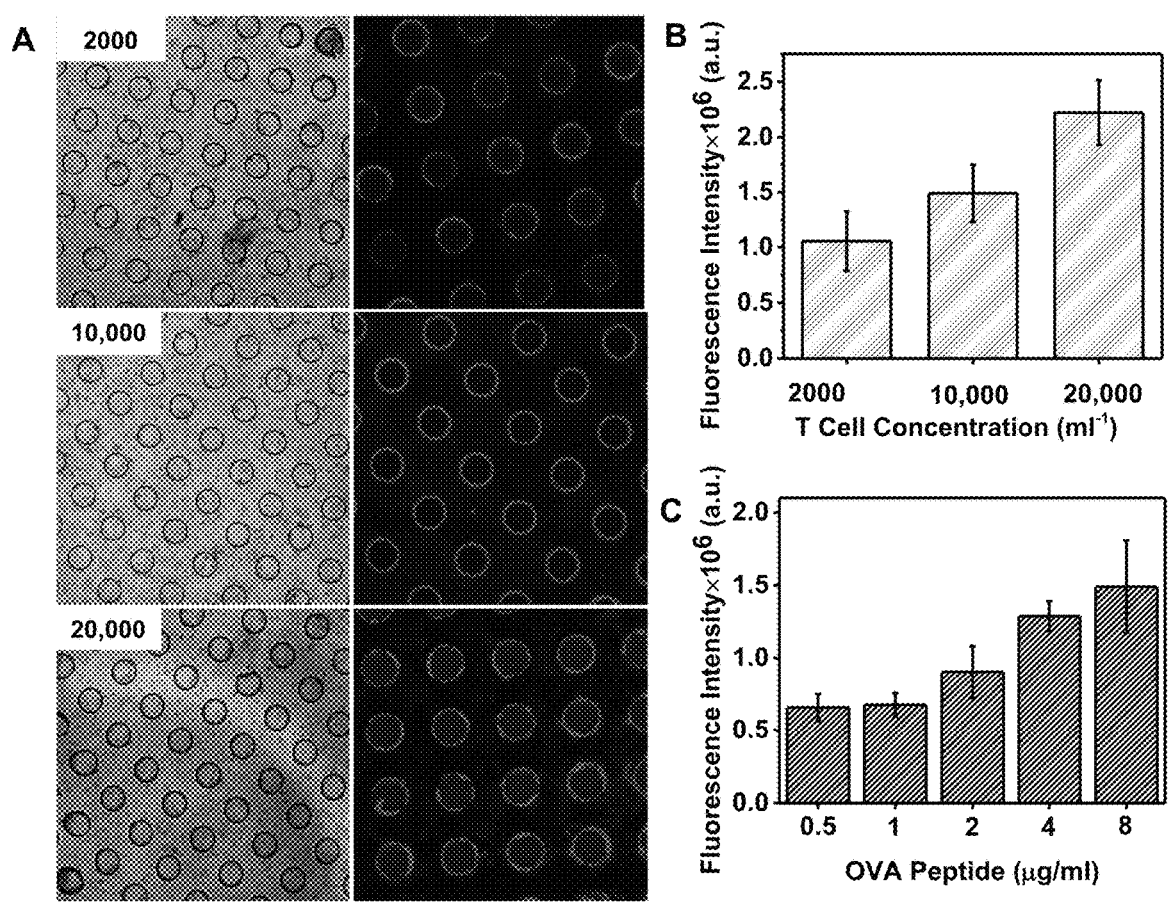
FIG. 12 shows detection of cytokine secretion at different T cell concentration based on microwell immunoassay. Brightfield and fluorescence images of OT-1 cells at different concentrations (A). Fluorescence intensity of immunoassay versus different T cell concentrations (B). Fluorescence intensity of immunoassay from T cells activated at different peptide concentrations (C).

FIG. 12 shows the detection of interferon-γ secreted by different numbers of OT-1 cells cultured in the microwells. OT-1 cells after stimulation by the OVA peptide (SINFEKL) can secrete cytokines including interferon-γ. Interferon-γ was captured on the bottom or side wall of the capture antibody pre-coated microwells. The brightfield image of the microwells with cells after adding different T cell numbers (2000, 10,000, 20,000) to the whole chip and the Texas Red fluorescence images of the same area after adding the OVA peptide (4 μg/mL) and an ELISA assay are shown in FIG. 12, panel A. The overall fluorescence intensity at each T cell concentration is calculated in FIG. 12, panel B. The fluorescence intensity was approximately 1.5 fold higher when the T cell concentration was increased by 10-fold, which means a larger amount of cytokines was secreted after increasing the T cell number. T cell stimulation and secretion under different OVA peptide concentration (0.5, 1, 2, 4, 8 μg/mL) are presented in FIG. 12, panel C. With the increase of the peptide concentration, the intensity of the interferon-γ fluorescence also increased, suggesting that (i) the activation of T cells can be determined by the peptide concentration and (ii) the amount of secreted cytokines can be higher from more activated T cells.

Figure 13:
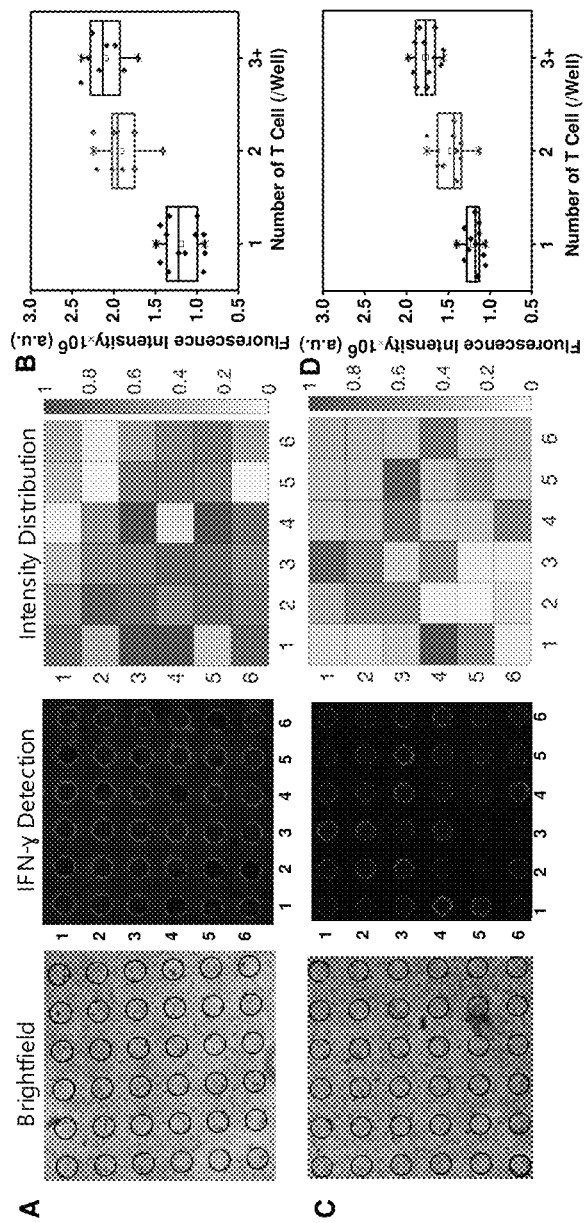
FIG. 13 shows single-cell analysis of cytokine secretion using microwell and number-dependency. Bright field and fluorescence image of cytokine detection based on B16-OVA/OT-1 cells co-culturing system (A). Fluorescence intensity versus different T cell number in each well based on B16-OVA/OT-1 cells co-culturing system (B). Fluorescence intensity of immunoassay in microwell chip based on OT-1/peptide condition (C). Fluorescence intensity versus different T cell number in each well based on OT-1/peptide condition (D).

The cytokine detection at a single cancer cell level was demonstrated in a capture antibody pre-coated microwell (FIG. 13). OT-1 cells were activated based on the recognition of OVA-derived peptide on the cancer cell membrane (FIG. 13, panel A). Red fluorescence in FIG. 13, panel A, shows that during cell-cell interactions inside microwells, OT-1 cells recognized the OVA peptide and secreted different amounts of cytokines. The levels of cytokines in each well were calculated and presented in a heat map. The heterogeneity of the cytokine signal indicates that the ELISA microwell assay was able to capture the cytokine released during cell-cell interactions and quantify the cytokine at a single cancer cell level. FIG. 13, panel B, demonstrates the fluorescence signal in each well versus number of T cells, indicating that the T cell-mediated cytokine secretion is also number-dependent when interacting with one cancer cell. The amount of the cytokine secreted from a single peptide-stimulated T cell is also shown in FIG. 13, panel C. According to the distribution in the heat map, the signal in the wells occupied with more than three T cells is over 1.5 times higher than that in the wells occupied with one T cell (FIG. 13, panel D), suggesting that the ELISA microwell assay can differentiate secretion from single T cells and determine the T cells with a higher ability of secretion and cytotoxicity.

EXEMPLIFICATION

Example 1

Two dimensional (2D) orthogonal-coordinated cell pattern was made by photolithography and molded from PDMS as reported before[14]. Multiple layers of polyelectrolytes poly(allylamine hydrochloride) (PAH) and poly(sodium 4-styrene sulfonate) (PSS) were prepared on the PDMS stamp and transferred onto hydrophobic modified glass slide. Fluorescein isothiocyanate (FITC) was linked to PAH to obtain better image of coordinated cell pattern under fluorescent microscopy. Cells were captured on the coordinated micro-patterns by electrostatic interaction with the polyelectrolyte, and were assigned to a unique index based on its location in two dimension (X and Y), which can be tracked in real time as captured cells remain at their locations in multiple handling steps. As an example, the responses of identical cells to X-ray radiation and chemotherapy have been determined with reactive oxygen species (ROS) assay, where ROS orange and green fluorescent dyes can stain cytoplasm and nucleus respectively. The procedures to perform identical cell analysis with MATLAB is listed as follows:
1) Crop the image into x pixels by y pixels for analysis;
2) Find cell boundaries in the cropped image;
3) Label cell index in order;
4) Calculate fluorescent intensity of each cell based on the RBG values inside each boundary;
5) Output fluorescent intensity and the corresponding index of each cell.

Example 2

A microwell array (100×100) was fabricated by photolithography and molded from PDMS with different diameters (30, 50 or 100 μm). The PDMS array with the microwells was then UV sterilized for 20 min and exposed to oxygen plasma for 30 seconds to make it hydrophilic. Microbubbles trapped in the microwells were removed by immersing the microwell into 1 mL medium under ultrasound agitation. B16-OVA melanoma and OT-1 cell occupancy rate and the number of cells in each well were calculated at different concentrations (10,000 to 80,000 cells/mL). The viability of cells seeded in the microwell array was tested with Calcein AM and propidium iodide (PI) to label live cells in green and dead cells in red. Cell adhesion and division were observed in order to evaluate cell viability and cytocompatibility of the PDMS matrix. Optical images of the same cancer cell were taken at different time points following cell seeding in the microwell array for 1, 2, 4, 8 and 20 hours.

For the co-culture experiments and longitudinal observations, B16-OVA cells were stained with CFSE, a green fluorescent dye, and incubated in microwells at 37° C. for 6 hours. Cell culture medium was then changed to RPMI and OT-1 cells were added into the microwells at the concentration of 80,000 cells/mL. The microwell array with the co-culturing system was immediately observed under a fluorescence microscope with incubation chamber (5% $CO_2$) and temperature control (37° C.). B16-OVA cells were located by green fluorescence; OT-1 cells were tracked from optical images. The interaction between B16-OVA and OT-1 cells was observed by time lapse for 6 hours, and photos were taken every 5 minutes.

Green fluorescence images derived from a 6-hour time lapse were input into MATLAB to calculate the intensity variation of each cell corresponding to the observation time. The area of each cell was measured using ImageJ and described using pixel. The number of OT-1 cells contacting with B16-OVA was counted via time-lapse video.

In some embodiments, the present disclosure relates to a method of determining a response of individual cells to stimuli, comprising:
(a) providing a plurality of cells distributed on a grid;
(b) exposing the plurality of cells to two or more stimuli; and
(c) measuring a response of one or more cells of the plurality of cells to the stimuli.

In some embodiments, two or more stimuli comprise a first stimulus and a second stimulus.

In some embodiments, the first stimulus is X ray radiation administered at a first dose and the second stimulus is X ray radiation administered at a second dose.

In some embodiments, at least one stimulus is a chemical compound.

In some embodiments, the grid comprises one or more fluorescent dyes.

In some embodiments, the grid comprises a plurality of microwells.

In some embodiments, each microwell comprises at least one polyelectrolyte.

In some embodiments, measuring a response of one or more cells of the plurality of cells to the stimuli comprises:
 (a) providing an image of the plurality of cells distributed on the grid;
 (b) locating boundaries of one or more cells in the image;
 (c) assigning an index to each of the one or more cells;
 (d) measuring a signal intensity within each of the one or more cell boundaries; and
 (e) recording the signal intensity and the index of each of the one or more cells.

In some embodiments, the signal is fluorescence.

In some embodiments, the present disclosure relates to a method of measuring interactions of individual cells, comprising:
 (a) providing a plurality of first cells distributed on a grid;
 (b) exposing the plurality of first cells to a plurality of second cells; and
 (c) measuring the interaction between one or more first cells and one or more second cells.

In some embodiments, measuring the interaction between one or more first cells and one or more second cells comprises:
 (a) providing an image of the plurality of first cells and the plurality of second cells distributed on the grid;
 (b) locating boundaries of one or more first cells in the image and, optionally, locating boundaries of one or more second cells in the image;
 (c) assigning a first index to each of the one or more first cells and, optionally, assigning a second index to each of the one or more second cells;
 (d) measuring intensity of a first signal within each of the one or more first cell boundaries and, optionally, measuring intensity of the second signal within each of the one or more second cell boundaries; and
 (e) recording the intensity of the first signal and the first index of each of the one or more first cells and, optionally, recording the intensity of the second signal and the second index of each of the one or more second cells.

In some embodiments, the image is generated using fluorescent time-lapse microscopy.

In some embodiments, the first signal and the second signal are the same.

In some embodiments, the first signal and the second signal are different.

In some embodiments, the first signal is fluorescence.

In some embodiments, the plurality of first cells comprises cancer cells and the plurality of second cells comprises T cells.

In some embodiments, the grid comprises a plurality of microwells, wherein each microwell is adapted to contain a total number of 2, 3, 4, 5, 6, 7, 8, 9, or 10 first cells and second cells. In some embodiments, each microwell is adapted to contain 1 to 3 first cells and 1 to 7 second cells.

In some embodiments, the grid comprises a plurality of microwells; each microwell comprises an inner surface; each microwell comprises a plurality of capture agents, each capture agent of the plurality of capture agents is immobilized on the inner surface of the microwell; and each capture agent of the plurality of capture agents is adapted to bind a molecule secreted by a first cell or a second cell.

In some embodiments, the capture agent is selected from the group consisting of a chemical compound, a protein, an antibody, a polycation, or a molecule comprising one or more positively charged groups or cell attracting moieties, that can bind to a molecule secreted by a cell. In some embodiments, the capture agent is a molecule that can specifically bind to antigens expressed on cell surfaces (such as folic acid).

In some embodiments, the capture agent is an antibody to anti-interferon-gamma (anti-IFN-γ).

In some embodiments, the molecule secreted by a first cell or a second cell is a cytokine.

In some embodiments, the cytokine is interferon-gamma (IFN-γ).

Exemplary Novel Features

Each cell is identified based on its location on a two dimensional coordinate.
Responses of over millions of cells can be tracked simultaneously and longitudinally.
Longitudinal observation of responses of identical cells to stimuli over time are detected.
Both cytotoxicity and genotoxicity can be assessed.
Low-cost and high throughput.

Exemplary Advantages and Improvements Over Existing Methods, Devices, or Materials Existing cellular assays cannot track cell behavior at single cell level.
Existing cellular assays do not allow observation of the same cell over time.
A high throughput method for rapid analyzing of identical cell behaviors and responses over time.
There is no existing identical cell analysis technique.
Easily and efficiently tracking identical cell after multiple treatments over time (longitudinal).
Acquiring statistic data and identical cell response at the same time.
Quantification of T cell cytotoxicity and cytokine release simultaneously in one device.
The first time using mathematic model to predict T cell cytotoxicity (cytokine secretion + killing efficiency).
Evaluation CD8 T cell killing efficiency based on different amount of T cells.
Co-location of T cell-cancer cell interaction and cytokine secretion.
Evaluation of T cell-cancer cell interaction at single cell level.
The microwell device can be based on low-cost materials (e.g., PDMS) with simple fabrication steps.
Large sample volume can be tested by screening millions of individual cells with a high throughput method.

Exemplary Commercial Applications

Drug screening and therapeutics validation.
Drug testing at point of uses.
Toxicity evaluation.
Environmental and radiation monitoring.
Cell biology and cancer biology research.

Single cell ELISA assay.
Immune cell activation screening.
Immunotherapeutic efficacy assessment.
Single cell proteomics.
Single cell RNA sequencing.
Personalized immunotherapy.
In vitro T cell engineering.
Identification of new biomarkers.
Methods, devices, and/or materials of the present disclosure can be used for assessing and predicting in-vitro therapeutic efficacy (e.g., immunotherapeutics) and toxicology at the single cell level.
Identification of new targetable biomarkers at the single cell level.
Discovery of new drugs and immune cell therapy (e.g., CAR-T cell).
Immune cell (e.g., T cell) engineering.
Personalized medicine, such as preclinical assessment of personalized immunotherapies.
Single cell drug screening for targeted drugs, immunotherapy drugs, and chemotherapy agents.
Immunosignature diagnostic for predicting vaccination performance.
Identification of reactive immune cells in autoimmune diseases.
Combination of single cell immune assay with single-cell RNA sequencing and single-cell proteomics.
Evaluation of cell-cell interactions and responses.
Study environmental effects (e.g., hypoxia, hyperoxygenation, pH change) on cells at the single cell level.

Incorporation by Reference

All US patents and US and PCT published patent applications cited herein are hereby incorporated by reference in their entirety as if each was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

REFERENCES CITED

1. Mervin, L. H.; Cao, Q.; Barrett, I. P.; Firth, M. A.; Murray, D.; McWilliams, L.; Haddrick, M.; Wigglesworth, M.; Engkvist, O.; Bender, A., Understanding Cytotoxicity and Cytostaticity in a High-Throughput Screening Collection. *ACS Chemical Biology* 2016, 11 (11), 3007.
2. Li, W.; Zhou, J.; Xu, Y., Study of the in Vitro Cytotoxicity Testing of Medical Devices. *Biomedical Reports* 2015, 3 (5), 617.
3. Colis, L. C.; Woo, C. M.; Hegan, D. C.; Li, Z.; Glazer, P. M.; Herzon, S. B., The Cytotoxicity of (−)-Lomaiviticin a Arises from Induction of Double-Strand Breaks in DNA. *Nature Chemistry* 2014, 6, 504.
4. Kroll, A.; Dierker, C.; Rommel, C.; Hahn, D.; Wohlleben, W.; Schulze-Isfort, C.; Göbbert, C.; Voetz, M.; Hardinghaus, F.; Schnekenburger, J., Cytotoxicity Screening of 23 Engineered Nanomaterials Using a Test Matrix of Ten Cell Lines and Three Different Assays. *Particle and Fibre Toxicology* 2011, 8 (1), 9.
5. Ruggeri, F. S.; Mahul-Mellier, A. L.; Kasas, S.; Lashuel, H. A.; Longo, G.; Dietler, G., Amyloid Single-Cell Cytotoxicity Assays by Nanomotion Detection. *Cell Death Discovery* 2017, 3, 17053.
6. Hosokawa, M.; Hayashi, T.; Mori, T.; Yoshino, T.; Nakasono, S.; Matsunaga, T., Microfluidic Device with Chemical Gradient for Single-Cell Cytotoxicity Assays. *Analytical Chemistry* 2011, 83 (10), 3648.
7. Lawrence, M. S.; Stojanov, P.; Polak, P., Mutational Heterogeneity in Cancer and the Search for New Cancer-Associated Genes. *Nature* 2013, 499, 214.
8. Raser, J. M.; Shea, E. K., Noise in Gene Expression: Origins, Consequences, and Control. *Science* 2005, 309 (5743), 2010.
9. Ryan, D.; Ren, K.; Wu, H., Single-Cell Assays. *Biomicrofluidics* 2011, 5 (2), 021501.
10. Wheeler, A. R.; Throndset, W. R.; Whelan, R. J.; Leach, A. M.; Zare, R. N.; Liao, Y. H.; Farrell, K.; Manger, I. D.; Daridon, A., Microfluidic Device for Single-Cell Analysis. *Analytical Chemistry* 2003, 75 (14), 3581.
11. Kim, H. S.; Devarenne, T. P.; Han, A., A High-Throughput Microfluidic Single-Cell Screening Platform Capable of Selective Cell Extraction. *Lab on a Chip* 2015, 15 (11), 2467.
12. Debs, B. E.; Utharala, R.; Balyasnikova, I. V.; Griffiths, A. D.; Merten, C. A., Functional Single-Cell Hybridoma Screening Using Droplet-Based Microfluidics. *Proceedings of the National Academy of Sciences* 2012, 109 (29), 11570.
13. Zhang, Y. S.; Aleman, J.; Shin, S. R.; Kilic, T.; Kim, D.; Mousavi Shaegh, S. A., Multisensor-Integrated Organs-on-Chips Platform for Automated and Continual in Situ Monitoring of Organoid Behaviors. *Proceedings of the National Academy of Sciences* 2017, 114 (12), E2293.
14. Xia, J.; Qiu, Y.; Xun, X.; Ma, L.; Guan, J.; Su, M., Single Cell Patterning for High Throughput Sub-Cellular Toxicity Assay. *Analytica Chimica Acta* 2018, 1007, 26.
15. Finn, O. J., Immuno-oncology: understanding the function and dysfunction of the immune system in cancer. Annals of Oncology 2012, 23 (8), viii6-viii9.
16. Couzin-Frankel, J., Cancer Immunotherapy. *Science* 2013, 342 (6165), 1432.
17. Mellman, I.; Coukos, G.; Dranoff, G., Cancer immunotherapy comes of age. *Nature* 2011, 480 (7378), 480-489.
18. Nishino, M.; Hatabu, H.; Hodi, F. S., Imaging of Cancer Immunotherapy: Current Approaches and Future Directions. *Radiology* 2018, 290 (1), 9-22.
19. Wei, S. C.; Duffy, C. R.; Allison, J. P., Fundamental Mechanisms of Immune Checkpoint Blockade Therapy. *Cancer Discovery* 2018, 8 (9), 1069-1086.
20. Sambi, M.; Bagheri, L.; Szewczuk, M. R., Current Challenges in Cancer Immunotherapy: Multimodal Approaches to Improve Efficacy and Patient Response Rates. Journal of Oncology 2019, 2019, 1-12.
21. Moya-Plana, A.; Herrera Gómez, R. G.; Rossoni, C.; Dercle, L.; Ammari, S.; Girault, I.; Roy, S.; Scoazec, J. Y.; Vagner, S.; Janot, F.; Eggermont, A. M. M.; Robert, C., Evaluation of the efficacy of immunotherapy for non-resectable mucosal melanoma. Cancer Immunology, Immunotherapy 2019, 68 (7), 1171-1178.
22. An, X.; Sendra, V. G.; Liadi, I.; Ramesh, B.; Romain, G.; Haymaker, C.; Martinez-Paniagua, M.; Lu, Y.; Radvanyi, L. G.; Roysam, B.; Varadarajan, N., Single-cell profiling of dynamic cytokine secretion and the phenotype of immune cells. PLoS One 2017, 12 (8), e0181904.
23. Mensali, N.; Myhre, M. R.; Dillard, P.; Pollmann, S.; Gaudernack, G.; Kvalheim, G.; Wälchli, S.; Inderberg, E. M., Preclinical assessment of transiently TCR redirected T cells for solid tumour immunotherapy. Cancer Immunology, Immunotherapy 2019, 68 (8), 1235-1243.
24. Calandri, M.; Solitro, F.; Angelino, V.; Moretti, F.; Veltri, A., The role of radiology in the evaluation of the immunotherapy efficacy. J Thorac Dis 2018, 10 (13), S1438-S1446.
25. Redman, J. M.; Steinberg, S. M.; Gulley, J. L., Quick efficacy seeking trial (QuEST1): a novel combination immunotherapy study designed for rapid clinical signal assessment metastatic castration-resistant prostate cancer. Journal for ImmunoTherapy of Cancer 2018, 6 (1), 91-98.
26. Tauriainen, J.; Gustafsson, K.; Göthlin, M.; Gertow, J.; Buggert, M.; Frisk, T. W.; Karlsson, A. C.; Uhlin, M.; Önfelt, B., Single-Cell Characterization of in vitro Migration and Interaction Dynamics of T Cells Expanded with IL-2 and IL-7. Front Immunol 2015, 6, 196-196.
27. Dura, B.; Servos, M. M.; Barry, R. M.; Ploegh, H. L.; Dougan, S. K.; Voldman, J., Longitudinal multiparameter assay of lymphocyte interactions from onset by microfluidic cell pairing and culture. Proc Natl Acad Sci USA 2016, 113 (26), E3599-E3608.
28. Sarkar, S.; Sabhachandani, P.; Stroopinsky, D.; Palmer, K.; Cohen, N.; Rosenblatt, J.; Avigan, D.; Konry, T., Dynamic analysis of immune and cancer cell interactions at single cell level in microfluidic droplets. Biomicrofluidics 2016, 10 (5), 054115-054115.
29. Xia, H.; Mathew, B.; John, T.; Hegab, H.; Feng, J., Microfluidic based immunosensor for detection and purification of carbonylated proteins. Biomedical Microdevices 2013, 15 (3), 519-530.
30. Kurschus, F. C.; Fellows, E.; Stegmann, E.; Jenne, D. E., Granzyme B delivery via perforin is restricted by size, but not by heparan sulfate-dependent endocytosis. Proceedings of the National Academy of Sciences 2008, 105 (37), 13799-13804.

What is claimed is:

1. A method of determining a response of individual cells to stimuli, comprising:
    (a) providing a plurality of cells distributed on a grid;
    (b) exposing the plurality of cells to two or more stimuli, wherein the two or more stimuli comprise a first stimulus, a second stimulus, and a chemical compound; the first stimulus is X-ray radiation at a first dose; and the second stimulus is X-ray radiation at a second dose; and
    (c) measuring a response to the two or more stimuli of one or more cells of the plurality of cells.

2. The method of claim 1, wherein the chemical compound is cytotoxic or genotoxic.

3. The method of claim 2, wherein the grid comprises one or more fluorescent dyes.

4. The method of claim 3, wherein the grid comprises a plurality of microwells.

5. The method of claim 4, wherein each microwell comprises at least one polyelectrolyte.

6. The method of claim 5, wherein measuring a response to the two or more stimuli of one or more cells of the plurality of cells comprises:
    (a) providing an image of the plurality of cells distributed on the grid;
    (b) locating boundaries of one or more cells in the image;
    (c) assigning an index to each of the one or more cells;
    (d) measuring a signal intensity within each of the one or more cell boundaries; and
    (e) recording the signal intensity and the index of each of the one or more cells.

7. The method of claim 6, wherein the signal is fluorescence.

8. The method of claim 2, wherein the grid comprises a plurality of microwells.

9. The method of claim 8, wherein each microwell comprises at least one polyelectrolyte.

10. The method of claim 2, wherein measuring a response to the two or more stimuli of one or more cells of the plurality of cells comprises:
    (a) providing an image of the plurality of cells distributed on the grid;
    (b) locating boundaries of one or more cells in the image;
    (c) assigning an index to each of the one or more cells;
    (d) measuring a signal intensity within each of the one or more cell boundaries; and
    (e) recording the signal intensity and the index of each of the one or more cells.

11. The method of claim 10, wherein the signal is fluorescence.

12. The method of claim 1, wherein the grid comprises one or more fluorescent dyes.

13. The method of claim 1, wherein the grid comprises a plurality of microwells.

14. The method of claim 13, wherein each microwell comprises at least one polyelectrolyte.

15. The method of claim 1, wherein measuring a response to the two or more stimuli of one or more cells of the plurality of cells comprises:
    (a) providing an image of the plurality of cells distributed on the grid;
    (b) locating boundaries of one or more cells in the image;
    (c) assigning an index to each of the one or more cells;
    (d) measuring a signal intensity within each of the one or more cell boundaries; and
    (e) recording the signal intensity and the index of each of the one or more cells.

16. The method of claim 15, wherein the signal is fluorescence.

* * * * *